(12) United States Patent
Mignon et al.

(10) Patent No.: US 11,732,084 B2
(45) Date of Patent: Aug. 22, 2023

(54) ANTI-MICROBIAL HYDROGEL

(71) Applicant: UNIVERSITEIT GENT, Ghent (BE)

(72) Inventors: Arn Mignon, Geraardsbergen (BE); Tom Gheysens, Ghent (BE); Sandra Van Vlierberghe, Sint-Niklaas (BE); Peter Dubruel, Ghent (BE)

(73) Assignee: UNIVERSITEIT GENT, Ghent (BE)

( * ) Notice: Subject to any disclaimer, the term of this patent is extended or adjusted under 35 U.S.C. 154(b) by 0 days.

(21) Appl. No.: 17/640,518

(22) PCT Filed: Sep. 11, 2020

(86) PCT No.: PCT/EP2020/075475
§ 371 (c)(1),
(2) Date: Mar. 4, 2022

(87) PCT Pub. No.: WO2021/048357
PCT Pub. Date: Mar. 18, 2021

(65) Prior Publication Data
US 2022/0325030 A1    Oct. 13, 2022

(30) Foreign Application Priority Data
Sep. 11, 2019  (EP) .................................... 19196659

(51) Int. Cl.
*A61L 26/00* (2006.01)
*C08G 18/75* (2006.01)
(Continued)

(52) U.S. Cl.
CPC ............ *C08G 18/756* (2013.01); *A61L 26/00* (2013.01); *A61L 26/008* (2013.01); *A61L 26/0052* (2013.01); *A61L 26/0066* (2013.01); *C08F 290/067* (2013.01); *C08G 18/4833* (2013.01); *C08J 3/075* (2013.01); *C08K 5/0058* (2013.01); *A61L 2300/106* (2013.01)

(58) Field of Classification Search
CPC .. A61L 26/005; A61L 26/0066; A61L 26/008; A61L 115/46; A61L 115/26; A61L 115/60; A61L 26/00
See application file for complete search history.

(56) References Cited

U.S. PATENT DOCUMENTS 4,359,558 A * 11/1982 Gould .................... A61L 15/60
                                                     521/905
4,769,013 A *  9/1988 Lorenz .................. A61L 15/225
                                                     424/78.25

(Continued)

FOREIGN PATENT DOCUMENTS

GB        2086927 A     5/1982

OTHER PUBLICATIONS

International Search Report & Written Opinion dated Dec. 7, 2020 in reference to co-pending European Patent Application No. PCT/2020/075475 filed Sep. 11, 2020.

*Primary Examiner* — Michael L Leonard
(74) *Attorney, Agent, or Firm* — Dinsmore & Shohl LLP (57) ABSTRACT

Hydrogels are provided that include an antimicrobial agent and a cross-linkable urethane-based polymer (CUP). Such hydrogels may be used for the controlled-release of antimicrobial agents as well as in the manufacturing of wound dressings. Wound dressings are provided that comprise a hydrogel as defined herein.

15 Claims, 3 Drawing Sheets

(51) Int. Cl.
*C08F 290/06* (2006.01)
*C08G 18/48* (2006.01)
*C08J 3/075* (2006.01)
*C08K 5/00* (2006.01)

(56) References Cited

U.S. PATENT DOCUMENTS

| | | | | |
|---|---|---|---|---|
| 5,156,601 A | * | 10/1992 | Lorenz | A61P 9/10 |
| | | | | 602/41 |
| 5,302,385 A | * | 4/1994 | Khan | C08G 18/65 |
| | | | | 424/445 |
| 2003/0203011 A1 | * | 10/2003 | Abuelyaman | C08F 290/142 |
| | | | | 424/445 |

* cited by examiner

ANTI-MICROBIAL HYDROGEL

CROSS REFERENCES TO RELATED APPLICATIONS

This application is a national-stage application under 35 U.S.C. § 371 of International Application No. PCT/EP2020/075475, filed Sep. 11, 2020, which International Application claims benefit of priority to European Patent Application No. 19196659.7, filed Sep. 11, 2019.

FIELD OF THE INVENTION

The present invention relates to the field of hydrogels; more in particular, hydrogels containing an antimicrobial agent. Specifically, the hydrogels of the present invention are characterized in comprising a cross-linkable urethane-based polymer (CUP). The present invention further provides uses of such hydrogels for the controlled-release of antimicrobial agents as well as uses thereof in the manufacturing of wound dressings. Finally, the present invention relates to wound dressings comprising a hydrogel as defined herein.

BACKGROUND TO THE INVENTION

Wound healing is a complex, fragile and dynamic process of replacing devitalized tissue. Chronic wounds can be very complex which implies that they have their own field of specialty within medicine. Wounds are often treated using wound dressings. The ideal wound dressing has strict requirements in order to realize optimal wound healing such as biocompatibility, the ability to provide a moist environment, the ability to remove excess exudate, being non-adhesive and easy removable and can be made in different sizes.

For those reasons, hydrogels gain more and more interest to be used in the preparation of wound dressings. Hydrogels are hydrophilic macromolecular networks, which can be produced by chemical or physical crosslinking of soluble polymers. Crosslinked 2-hydroxyethyl methacrylate (HEMA) hydrogels have been amongst the first to be used in numerous biomedical applications, such as drug carriers, absorbable sutures, osteoporosis, etc. Hydrogels are particularly interesting for use in wound healing due to the fact that they can control the loss of fluids and liquids from the body and they maintain the wettability and moist in the wound zone, by uptake of excess exudate, and release thereof if the wound is too dry. Moreover, they possess a tissue-like structure and compatibility. Finally, most hydrogels are transparent and allow visual inspection of the wound without removal of the dressings.

It is an advantage in the field of wound dressings to incorporate an anti-microbial agent, such as iodine within said wound dressing, to reduce the risk of infections, this can for example be done by soaking the dressings in an iodine solution. However, the current problem with iodine as antibacterial agent in wound healing is its uncontrollable and too fast release. The consequence is that the dressings need to be changed often (twice a day) for obtaining a continuous antibacterial effect. This excessive use of antibacterials is also what causes bacterial resistance.

We have now found a solution to the above stated problems by means of a hydrogel comprising a cross-linkable urethane-based polymer (CUP), as further defined herein below. These polymers are characterized in being cross-linkable and moreover have a backbone which is capable of complexing iodine within the hydrogel. In doing so, the release of the anti-microbial agent can be significantly prolonged even up to several days. Wound dressings prepared using such hydrogels have been found to closely mimic the extracellular matrix and are still breathable allowing the wounds to better heal. Moreover, the hydrogels/wound dressings strongly adhere to the wound, thereby conforming to the shape of the wound, yet they do not stick in the wound and are easily removable. In addition, the wound dressings of the present invention can also be easily cut to the required size.

SUMMARY OF THE INVENTION

In a first aspect, the present invention provides a hydrogel comprising:
an antimicrobial agent, and
a cross-linkable urethane-based polymer (CUP) represented by formula (I)

wherein:
each occurrence of X and Y is independently a moiety comprising one or more of the following: acrylate groups, (multi)methacrylate groups, (multi)acrylate group, thiolactones and thiol-ene crosslinkable groups;
each occurrence of Spacer is independently selected from the list comprising: oligo(ethylene oxide), oligo(propylene oxide), oligo(caprolactone), oligo(lactide) and oligo(glycolide);
m and n are each independently from 1-6;
p is from 1-10; and
each occurrence of Backbone is independently selected from the list comprising poly(ethylene glycol) (PEG), poly(vinyl pyrrolidone) (PVP), poly(N-vinyl caprolactam) (PNVCL), or a combination thereof.

In a preferred embodiment, said spacer is oligo(ethylene) oxide.

In a specific embodiment, the hydrogel of the present invention comprises a polymer combination of a cross-linkable urethane-based polymers (CUP) represented by formula (I); wherein at least one of said polymers has a backbone of PEG and at least one other polymer has a backbone of PVP, PNVCL, or a combination thereof.

In a particular embodiment, said polymer combination is selected from a copolymer, a polymer blend, or a combination of different polymer layers (i.e. multilayer stack).

In another specific embodiment of the present invention, one or more of the following applies:

said PEG has a molecular weight of about 400 g/mol (PEG400) to about 20000 g/mol (PEG20k);
said PVP has a molecular weight of about 400 g/mol (PVP400) to about 365000 g/mol (PVP365k), and/or
said PNVCL has a molecular weight of about 400 g/mol (PNVCL400) to about 2500000 g/mol (PNVCL-2.5M).

The present invention also provides a hydrogel as defined herein, further comprising PVP, PEG, PNVCL or a combination thereof.

In a very specific embodiment of the present invention, said antimicrobial agent is an Iodine-based agent.

The hydrogel of the present invention may be in any suitable form, such as for example in the form of a sheet, a membrane, a fiber, a particle or a scaffold.

In a further embodiment, the hydrogel of the present invention may be crosslinked, such as chemically crosslinked.

In another aspect, the present invention provides the use of the hydrogel as defined herein for controlled-release of antibacterial agents. Hence, the present invention also provides the use of the hydrogel as defined herein in the manufacturing of a wound dressing.

In a further aspect, the present invention provides a wound dressing comprising a hydrogel according to the present invention.

The present invention also provides a hydrogel as defined herein or a wound dressing as defined herein for use in human and/or veterinary medicine; more in particular for use in skin care and/or wound care.

BRIEF DESCRIPTION OF THE DRAWINGS

With specific reference now to the figures, it is stressed that the particulars shown are by way of example and for purposes of illustrative discussion of the different embodiments of the present invention only. They are presented in the cause of providing what is believed to be the most useful and readily description of the principles and conceptual aspects of the invention. In this regard no attempt is made to show structural details of the invention in more detail than is necessary for a fundamental understanding of the invention. The description taken with the drawings making apparent to those skilled in the art how the several forms of the invention may be embodied in practice.

DETAILED DESCRIPTION OF THE INVENTION

As already detailed herein above, the present invention provides a hydrogel comprising:

an antimicrobial agent, and a cross-linkable urethane-based polymer (CUP) represented by formula (I)

wherein:
each occurrence of X and Y is independently a moiety comprising one or more of the following: acrylate groups, (multi)methacrylate groups, (multi)acrylate group, thiolactones and thiol-ene crosslinkable groups;
each occurrence of Spacer is independently selected from the list comprising: oligo(ethylene oxide), oligo(propylene oxide), oligo(caprolactone), oligo(lactide) and oligo(glycolide);
m and n are each independently from 1-6;
p is from 1-10; and
each occurrence of Backbone is independently selected from the list comprising poly(ethylene glycol) (PEG), poly(vinyl pyrrolidone) (PVP), poly(N-vinyl caprolactam) (PNVCL), or a combination thereof.

In the context of the present invention, the term "antimicrobial agent" is meant to be an agent that kills or at least stops the growth of microorganisms, such as bacteria and fungi. While all kinds of antimicrobial agents may suitably be used within the context of the present invention, the invention is particularly suitable for use with antimicrobial agents which can be complexed with the polymers of the hydrogel. Such antimicrobials are for example Iodine-based agents, and suitable salt forms thereof.

Hence, in a further embodiment of the present invention, said antimicrobial agent is an Iodine-based agent. Iodine is a highly effective topical antimicrobial agent which has been used clinically for decades. It has a broad spectrum of antimicrobial activity with efficacy against bacteria, mycobacteria, fungi, protozoa and viruses and can be used to treat both acute and chronic wounds. Iodine may be used as such, however, it could also be used in the form of an iodophore, which is a preparation that binds iodine to a solubilizing agent or carrier. Amongst these preparations, povidone iodine (PVP-I), a chemical complex of polyvinylpyrrolidone and elemental iodine, is very commonly used. Povidone-iodine can be loaded into polymeric hydrogels and depending on the composition of the hydrogel its release profile may be adjusted.

In the context of the present invention, the term "urethane-based polymer" is meant to be a polymeric agent containing one or more carbamate or urethane links. A carbamate is an organic compound derived from carbamic acid ($NH_2COOH$), and as such a carbamate link may be generally represented as follows:

wherein each wavy line represents an attachment point to the remainder of the polymer molecule. In the context of the present invention, the claimed polymers contain at least one carbamate linker, however, they may also contain several carbamate linkers such as 2, 3, 4, or 5 carbamates.

The term "urethane- and/or urea-containing moiety" as used herein is meant to be a moiety composed of organic units joined by carbamate (urethane) links, i.e. —NH—(C=O)—O—; and/or urea links, i.e. —NH—(C=O)—NH—. Hence, in one embodiment, this moiety may contain only urethane linkers. Alternatively, this moiety may contain only urea linkers. Moreover, this moiety may also contain a combination of urethane and urea linkers.

As detailed herein above, the urethane-based polymers of the present invention may include different types and numbers of end-groups, including acrylate groups, (multi)methacrylate groups, (multi)acrylate group, thiolactones and thiol-ene crosslinkable groups. Alternatively, the urethane-based polymers may also include (meth)acrylamide groups. Hence, the compounds of the present invention may also be termed as such, for example, in the event of X and/or Y being selected as acrylate groups, the polymers may be termed acrylate end-capped urethane-based polymers (i.e. AUP).

Hence, in a specific embodiment, the present invention also provides an acrylate end-capped urethane-based polymer of formula (II)

wherein m, n, p, Spacer and Backbone are defined as herein above. Hence, each occurrence of crosslinkable urethane-based polymer (CUP) in the current application can be replaced by urethane-based polymer (UP).

The term "acrylate end-capped" as used herein means that the acrylate groups of the molecules of the invention are the polymer endgroups.

In the context of the present invention, the term "acrylate" is meant to include salts, esters and conjugate bases of acrylic acid and it derivatives. Acrylates contain vinyl groups, i.e. 2 carbon atoms double bonded to each other, directly attached to a carbonyl carbon. An acrylate moiety is typically represented as follows:

wherein R represents —H in the event of acrylates or an alkyl group such as for example a methyl (—CH$_3$) moiety, in the event of methacrylates. The (meth)acrylate groups according to the present invention are attached to the remainder of the polymer via the —O— linker, such that the double bonded carbon atom faces outwardly of the molecules.

In a specific embodiment, X and/or Y, may be selected to be a functional group that is able to or susceptible to thiol-ene cross-linking (i.e. a thiol-ene cross-linkable group). Preferably, the functional groups comprise functional groups able to or susceptible to thiol-ene crosslinking. The functional groups comprise for example meth(acrylate)

(II)

wherein m, n, p, Spacer and Backbone are defined as herein above.

In an alternative embodiment, the present invention also provides a urethane-based polymer (UP) of formula (I)

functional groups, meth(acrylamide) functional groups, norbornene functional groups, vinyl ether functional groups, vinylester functional groups, allyl ether functional groups, propenyl ether functional groups and/or alkene functional

(I)

groups and/or N-vinylamide functional groups. Particularly preferred functional groups comprise norbornene functional groups and/or vinylether functional groups.

The use of thiol-ene cross-linkable groups in the urethane-based polymers of the present invention, may be advantageous, since these can reduce the brittleness of the end products and result in a more homogeneous network formation.

In the context of the present invention, the term "spacer" is meant to be a moiety intended to provide a (flexible) hinge between 2 other elements of the molecule in which it is included, thereby spatially separating said elements. In the context of the present invention, a spacer may be present as indicated in Formula I. In the context of the invention, any type of suitable moiety may be used as a spacer, however, it is preferably selected from the list comprising oligo(ethylene oxide), oligo(propylene oxide), oligo(caprolactone), oligo(lactide) and oligo(glycolide):

wherein n is 1-6

In a preferred embodiment, said spacer is oligo(ethylene) oxide.

Moreover, as evident from Formula I, the spacer is present on both sides of the molecule, in which m and n are independently from 1-6. This means that where a spacer is selected to be for example oligo(ethylene oxide) and n is for example 2, the spacer thus comprises 2 ethylene oxide moieties. Moreover, the left and right parts of the claimed molecules need not to be symmetrical, meaning that each spacer and the number of monomeric units within each spacer may be selected independently from each other. Nevertheless, in a preferred embodiment, the left and right parts of the claimed molecules are symmetrical, meaning that both sides of the molecule contain the same spacer containing the same number of monomeric units.

As evident from formula I, the claimed molecules also encompass a backbone, which may be selected from the list comprising: poly(ethylene glycol) (PEG), poly(vinyl pyrrolidone) (PVP), poly(n-vinyl caprolactam) (PNVCL), or a combination thereof:

Poly(ethylene glycol) (PEG)

poly (n-vinly pyrrolidone) (PVP)

poly (n-vinly caprolactam) (PVNCL)

In the context of the present invention, it was found that a polymer combination including at least one PEG-based polymer was particularly preferred. In particular, it was found that PEG polymers may contribute in the complexation of anti-microbial agents, such as iodine. Therefore, in a particular embodiment, the present invention provides a polymer combination of a cross-linkable urethane-based polymers (CUP) represented by formula (I); wherein at least one of said polymers has a backbone of PEG and at least one other polymer has a backbone of PVP, PNVCL, or a combination thereof. In a particular embodiment, said polymer combination may be selected from a copolymer, a polymer blend, or a combination of different polymer layers (i.e. multilayer stack).

In the context of the present invention, the term "polymer blend" is meant to be a polymer mixture in which two or more polymers of a different nature are blended. In the context of the present invention, a copolymer is meant to be a polymeric molecule comprising at least 2 different types of monomeric subunits. This means that the present invention also provides a cross-linkable urethane-based polymers (CUP) represented by formula (I); wherein at least one part of said polymer has a backbone of PEG and at least one other part of said polymer has a backbone of PVP, PNVCL, or a combination thereof.

In another specific embodiment of the present invention, one or more of the following applies:
said PEG has a molecular weight of about 400 g/mol (PEG400) to about 20000 g/mol (PEG20k);
said PVP has a molecular weight of about 400 g/mol (PVP400) to about 365000 g/mol (PVP365k), and/or
said PNVCL has a molecular weight of about 400 g/mol (PNVCL400) to about 2500000 g/mol (PNVCL2.5M).

In other words, the backbone of the claimed molecules may be selected from any PEG having a molecular weight between 400 g/mol and 20000 g/mol; or from any PVP having a molecular weight between 400 g/mol and 365000 g/mol a; or from any PNVCL having a molecular weight of 400 g/mol and 2500000 g/mol; or any combination thereof, such as a combination of PEG and PVP, a combination of PEG and PNVCL, a combination of PVP and PNVCL, or a combination of PEG, PVP and PNVCL. Each of said combinations may thus be in the form of a polymer blend, e.g. polymers having a PEG backbone blended together with polymers having a PVP backbone. Alternatively said combinations may be in the form of a copolymer, e.g. polymers having a mixed PEG/PVP backbone; wherein some occurrences of Backbone are selected to be PEG and other occurrences of Backbone are selected to be PVP. The same reasoning also applies for other combinations of polymers e.g. PEG/PNVCL or PVP/PNVCL or PEG/PVP/PNVCL.

In some embodiments of the present invention, the claimed hydrogels may further comprise PVP, PEG, PNVCL or a combination thereof. Specifically, apart from the claimed CUP polymers, the hydrogel may further be supplemented with free PVP, PEG, PNVCL or a combination thereof. Such components may for example be blended with the CUP polymers during preparation of the hydrogel. A further advantage of supplementing the hydrogels with free PVP, PEG, PNVCL or a combination thereof, is their property of further complexing the anti-microbial agents (e.g. iodine), whereby the degree of complexation can be easily adjusted depending on the intended application. As the degree of complexation, amongst others, influences the release rate, the release profile of the hydrogels can be adjusted according to the needs, by varying the amount of free PVP, PEG, PNVCL or a combination thereof.

The advantage of the CUPs of the present invention is that they are electrospinnable, even in the presence of the anti-microbial agent. This is particularly advantageous in the preparation of wound dressings, in that these electrospun materials can be made in any kind of format, such as for example in the form of a sheet, a membrane, a fiber, a particle, a scaffold, . . . . Electrospun materials provide an excellent environment to promote wound healing. Nanofibers/microfibers generated by the electrospinning technique offer a high surface-to-volume ratio, show good porosity levels, allow gaseous exchange and mimic the natural extracellular matrix. Additionally, they can be made in any shape that suits the wound. All these characteristics promote cell respiration, skin regeneration, haemostasis, exudate removal and moisture retention while the interconnected nano/microporosity prevents microbial infiltration. The formation of fibers via electrospinning depends on several parameters including the viscosity, the needle-to-collector distance, the flow rate and the applied voltage, etc. These parameters influence the morphology of the obtained fibers.

In a further embodiment of the present invention, the CUPs of the present invention may also be processed using other techniques such as extrusion-based 3D-printing.

Cross-linkable urethane-based polymers (CUP) are very interesting in this respect, due to their ability to cross-link upon Ultra-Violet (UV) irradiation in solid state. In addition, they exhibit high mechanical strength (up to 0.6 MPa in swollen state for precursors cross-linked in a 30 wt % aqueous solution) and biocompatibility. These hydrogel precursors can be based on different polymer backbones and cross-linking in the solid state is promoted by the presence of a flexible spacer which is linked to the backbone polymer by means of a di-isocyanate (such as isophorone di-isocyanate (IPDI)). In a particular embodiment, the material may be chemically cross-linked, such as for example through irradiation (e.g. UV), thermal crosslinking, redox cross-linking, electron-beam cross-linking, etc.

As already explained herein before, the hydrogels of the present invention are particularly suitable for complexing anti-microbial agents, such as iodine-based agents. Moreover, due to their tunable release properties, they are highly suitable for the controlled-release of such anti-microbial agents. For similar reasons, the claimed hydrogels are also highly suitable for use in skin and/or wound care, or for the coating of for example medical devices such as stents.

In a further aspect, the present invention thus also provides a wound dressing comprising a hydrogel as defined herein. Wound dressings comprising or being made of a hydrogel as defined herein can absorb and retain the wound exudates, which promote fibroblast, endothelial and/or epithelial proliferation; and keratinocyte migration. These processes are highly relevant for complete epithelialization and healing of the wound. In addition, the tight mesh size of hydrogel structures protects the wound from infection and prevents microorganism and bacteria to reach the wound area. However, hydrogel structures allow transporting bioactive molecules e.g. antibiotics, and pharmaceuticals to the wound center. Such molecules can be entrapped into hydrogel networks during gelling process, while these molecules can be exchanged while absorbing the wound exudates during the sustainable release process after contacting the hydrogels with the wound surface. The significant tissue-like water content of hydrogels provides the needed flexibility and elasticity to adapt to wounds located in different body sites.

The present invention also provides a hydrogel as defined herein or a wound dressing as defined herein for use in human and/or veterinary medicine; more in particular for use in skin care and/or wound care; such as in particular for the treatment of wounds.

EXAMPLES

Example 1

Material and Methods

The composition and nomenclature of the hydrogel sheets are provided in Table 1.

TABLE 1

Overview of material composition for hydrogel sheets

| Name | AUP/PEG* | AUP (wt %) | PVP 360k (wt %) | ddH$_2$O (wt %) |
| --- | --- | --- | --- | --- |
| 2k Blank | AUP2k | 30 | 0 | 70 |
| 2k PVP | AUP2k | 30 | 2.4 | 67.6 |
| 10k Blank | AUP10k | 30 | 0 | 70 |
| 10k PVP | AUP10k | 30 | 2.4 | 67.6 |
| 20k Blank | AUP20k | 30 | 0 | 70 |
| 20k PVP | AUP20k | 30 | 2.4 | 67.6 |

Figure 1:
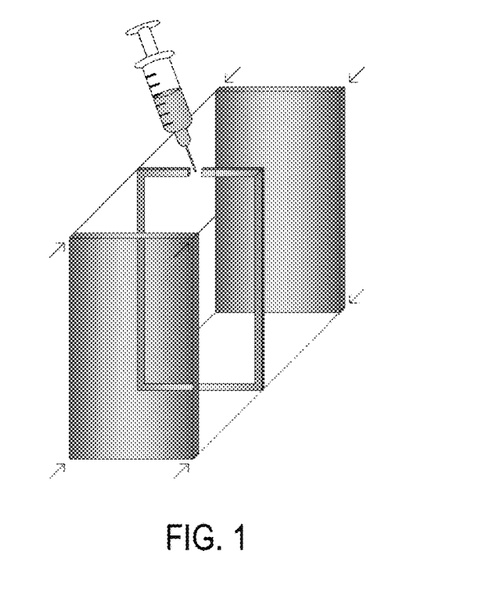
FIG. 1: Illustration of the preparation of a hydrogel sheet according to an embodiment of the invention.

*AUP/PEG: Acrylate end-capped urethane-based polymers having a 2k-20k PEG Backbone The samples were prepared by pouring the solution in between two glass plates, which were covered with Teflon release foil and separated by a spacer (as illustrated in FIG. 1).

The hydrogel samples were UV-cured by placing them for 1 hour between 2 high performance UV-A transilluminators manufactured by AppliTek NV, with wavelengths in the range of 315-400 nm. The intensity of the upper and lower lamps was respectively 6.8 mW/cm$^2$ and 6.2 mW/cm$^2$. Prior to curing, the intensity of both lamps is verified by measuring with a radiometer and probe UV-A (0-200 mW/cm$^2$), type RM12 manufactured by Opsytec Dr. Gröbel.

A Lugol's solution (iodine-based anti-microbial agent) was used to complex iodine to hydrogel samples by soaking them after cross-linking. The ratio of KI:I$_2$ (Potassium Iodine: Iodine) is 1:1.576, corresponding to the ratio in Fixanal iodine standard 189. The solution was prepared at 4 different concentrations as follows:

Series 1 (1%): 357.35 mg KI+226.82 mg I2 in 50 ml ddH2O
Series 2 (0.2%): 6 ml of series 1+24 ml ddH2O
Series 3 (0.05%): 1.5 ml of series 1+28.5 ml ddH2O
Series 4 (0.01%): 300 µl of series 1+29.7 ml ddH2O It should be noted that the concentrations are expressed in % of I, which corresponds to 10 mg/ml iodine.

The ultrasonic bath was used to aid the dissolving process of iodine and potassium iodide in water, ethanol or PBS. The Branson 2510 Ultrasonic Cleaner was used for 1 hour at a frequency of 40 kHz.

Hydrogel samples were saturated in double distilled $H_2O$ in an incubator at 20° C., the time to reach saturation depends on the molecular weight of the backbone, all are saturated after 72 hours. Hydrogel disks (Φ=16 mm, h=1 mm) were placed in a petri dish (0=55 mm) in triplicates and were soaked in 10 ml of the Lugol's solution (concentration of 1%, 0.2%, 0.05% or 0.01%) for 1 hour. After soaking, the samples were put between glass plates for 24 h in a refrigerator of 7° C. and subsequent were dried in a vacuum oven (at 20° C.) or desiccator for 3 hours.

A PANalytical esilon3-XL with corresponding epsilon 3 software was used to determine the iodine content in hydrogel samples. The system parameters are a voltage of 12 kV, a current of 0.974 mA, an acquisition time of 200 seconds and an A1-50 filter.

The calibration series is made by physical gelation of gelatin B. Table 2 provides an overview of the blends used for the standard series. The standard series was produced using a $KI/I_2$ stock solution.

TABLE 2

Standard series used to produce calibration curve for XRF measurements.

| $KI/I_2$ stock (µl) | $H_2O$ (µl) | Total Volume (ml) | Concentration I (mg/ml) |
|---|---|---|---|
| 0 | 3000 | 3 | 0 |
| 30 | 2970 | 3 | 1 |
| 60 | 2940 | 3 | 2 |
| 150 | 2850 | 3 | 5 |
| 300 | 2700 | 3 | 10 |
| 600 | 2400 | 3 | 20 |
| 1050 | 1950 | 3 | 35 |

TABLE 3

Iodine concentration of AUP Blends soaked in 0.2% Lugol's solution (expressed in mg/ml).

| | AUP2k | AUP10k | AUP20k | Iso-Betadine gel 10% |
|---|---|---|---|---|
| Blank | 20.8 ± 5.6 | 32.5 ± 6.2 | 29.4 ± 7.4 | 24.2 ± 0.6 |
| PVP | 33.6 ± 5.4 | 36.6 ± 7.6 | 20.5 ± 8.2 | |

764.47 mg KI+453.63 mg I2+10 ml ddH2O was first sonicated for 1 h and subsequently put in an oil bath at 40° C. until completely dissolved. After diluting, the standard series was heated to 40° C., next 313.8 mg Gelatin B and 26.9 mg of PVP360 was added to each solution while stirring. Solvent casting (cylindrical, Φ=16 mm, thickness=1 mm) was used to produce the standard series in triplicates.

Results

A) Anti-Bacterial Tests and the Effect of PVP

The antibacterial tests were performed in triplicate on 16 mm disks. Several categories were tested:
  PVP-I loaded hydrogels: (2k Blank, 2k PVP, 10k Blank, 10k PVP, 20k Blank, 20k PVP)
  Negative control samples: not incubated in iodine (2k Blank, 2k PVP and 20k Blank)
  Positive reference samples: Iso-Betadine Tulle 10% (IBT 10%)

Agar plates were prepared from Tryptic Soy Agar, a medium that supports the growth of a variety of microorganisms providing enough nutrition, named TSA plates. The plates were inoculated with *Staphylococcus aureus* Mu50 which was cultured in Mueller-Hinton Broth at 37° C. The samples were placed in the centre of the TSA plate, after which the plates were incubated for 24 hours at 37° C. The inhibition zone (IZ) was measured as the diameter of the total zone of inhibition in 2 perpendicular directions on black paper with a ruler, rounding to nearest millimetre. Samples showing antibacterial effect, thus an inhibition zone, after 24 hours were transferred to fresh TSA plate inoculated with *Staphylococcus aureus* Mu50 and were incubated for another 24 hours.

The evaluation is performed using an agar disk diffusion assay, also called the Kirby Bauer test. The test is quick and inexpensive and thus ideal for determining the antibacterial potency of the (povidone) iodine loaded hydrogel sheets. Besides the PVP-I loaded hydrogel sheets, hydrogel disks (2k Blank, 2k PVP and 20k Blank) were tested without iodine incubation as a negative control and IBT 10% was used as a positive control. The samples were placed on TSA plates, which were inoculated with *Staphylococcus aureus* 1 day prior to the measurement. After 24 hours, the diameter of the inhibition zone (IHZ) is measured.

As expected, the negative controls do not exhibit an antibacterial effect in the absence of an antibacterial compound. In contrast, hydrogel sheets with and without PVP, both incubated in iodine solution, showed inhibition zones after 24 hours. The addition of PVP had no significant effect on the inhibition zone, indicating the relevant complexation potential of PEG with iodine. The results are presented in FIG. 2. This figure also shows the total mass of iodine that has been released into PBS by UV-visible spectroscopy.

Figure 2:
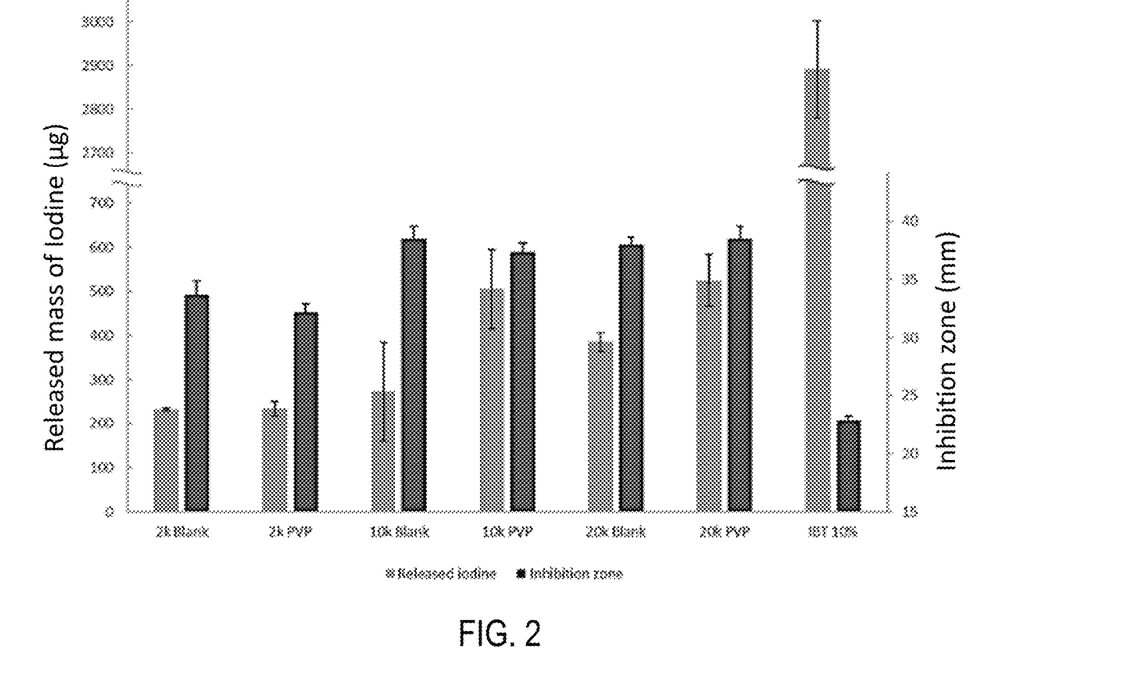
FIG. 2: The mass of total released iodine after 48 hours (in µg) and diameter of the inhibition zone after 24 hours (in mm) of hydrogel samples and Iso-Betadine Tulle 10%. The released mass of iodine in IBT 10% is 2 988±33 µg (not visible on graph). Error bars indicate standard deviation (n=3).

From the graph, a similar trend can be observed between the IHZ and the leached mass of iodine in the hydrogel samples. The IHZ and released mass of iodine is significantly lower in AUP2k than AUP10k and AUP20k. After 24 hours, a darker colour was observed in AUP2k compared to AUP10k and AUP20k (data not shown). The denser network in AUP2k resulted in a higher retention of iodine and subsequently a lower IHZ. The IHZ of AUP10k and AUP20k are similar.

The IHZ of IBT 10% was 22.8±0.4 mm, being significantly lower than the PVP-I loaded hydrogels, while the released mass of iodine is 2 988±33 µg which is significantly higher than the PVP-I loaded hydrogels. With a half-life of only 37 seconds in PBS, the application of IBT 10% resulted in a burst release. Even though the released mass of iodine was extensive but rapid, the resulting antibacterial effect was limited compared to the PVP-I loaded hydrogels which have a prolonged release, and thus prolonged efficacy.

B) Evidence of Prolonged Release of Anti-Bacterial Agent

The UVIKONXL, an ultraviolet-visible spectrophotometer from BIO-TEK instruments was used to measure the absorbance of a solution for wavelengths in the range of 180-900 nm. A wavelength of 352 nm was used to determine the concentration of iodine leached from an iodine loaded hydrogel in PBS. The output was provided by LabPower software.

TABLE 4

The standard series used to produce the calibration curve for UV-spectrometry.

| KI/I$_2$ stock (μl) | PBS stock (μl) | Total Volume (ml) | Concentration I (mg/ml) |
|---|---|---|---|
| 0 | 10000 | 10 | 0 |
| 50 | 9950 | 10 | 0.01 |
| 100 | 9900 | 10 | 0.02 |
| 200 | 9800 | 10 | 0.05 |
| 500 | 9500 | 10 | 0.1 |
| 1000 | 9000 | 10 | 0.2 |
| 2500 | 7500 | 10 | 0.5 |
| 5000 | 5000 | 10 | 1 |
| 10000 | 0 | 10 | 2 |

Table 4 provides an overview of the blends used for the standards series, which was produced using the following stock solutions:

PBS stock: 8.00 g NaCl+0.20 g KCl+1.44 g Na$_2$HPO$_4$+ 0.24 g KH$_2$PO$_4$+1 Liter ddH2O. The pH was measured to be 7.5 with pHenomenal pH 1100 L pH meter KI/I$_2$ stock: 71.47 mg KI+45.36 mg I2+50 ml PBS stock The KI/I$_2$ stock was first sonicated for 1 h and subsequently put in an oil bath at 40° C. until completely dissolved.

The calibration curve was valid for concentrations within the range of 0-0.2 mg/ml (absorbance<2). If a higher concentration was observed with the measurements, the solution was diluted with PBS with a factor until the absorbance was less than two.

Triplicates of the samples were placed in separate vials and 4 ml of PBS buffer (T=40° C.) was added. The vials were placed in an incubator at a temperature of 40° C. The absorbance of the solvent was measured at time points 1, 4, 24 and 48 hours. Before transferring 3 ml of the solvent to the cuvette, the vials were shaken. After measuring, the solvent was added back to the vials.

The absorbance was converted to the concentration of PBS using the following formula, where A$_t$=absorbance at λ=352 nm at t hours and Ct=concentration of iodine in mg/ml at t hours.

$$C_t(\text{mg/ml}) = \frac{-4.39 + \sqrt{(4.39)^2 - 4 \times 26.984 \times (-0.0325 - A_t)}}{2 \times 26.984}$$

The released mass of iodine can be calculated by converting the concentration of iodine in the PBS to mass as mI (mg)=4 ml Cmax (mg/ml). The relative concentration at time=t hours (Crel,t) is calculated as follows, where Ct (expressed in mg/ml) is the (absolute) concentration of PBS at time t and Cmax is the maximal concentration of PBS (expressed in mg/ml):

$$C_{rel,t} = 1 - \frac{C_t}{C_{max}}$$

The half-life of the samples is determined using non-linear regression. To determine the best possible fit, the method of least squares was used between the relative concentrations and an exponential trendline. The solver tool in Microsoft Excel was used to determine the best values of a and k in the trendline with equation y=α exp(−k*t) by minimizing the sum of the squared residuals. The half-life (t1/2) and the measure of good fit, the standard error of the regression (S), were calculated as follows:

$$t_{1/2} = \frac{\ln(2)}{k}$$

$$S = \sqrt{\frac{SS}{n - p - 1}}$$

With SS being the sum of the squared residuals, n being the number of datapoints (5) and p being the degrees of freedom in the model (2).

Figure 3:
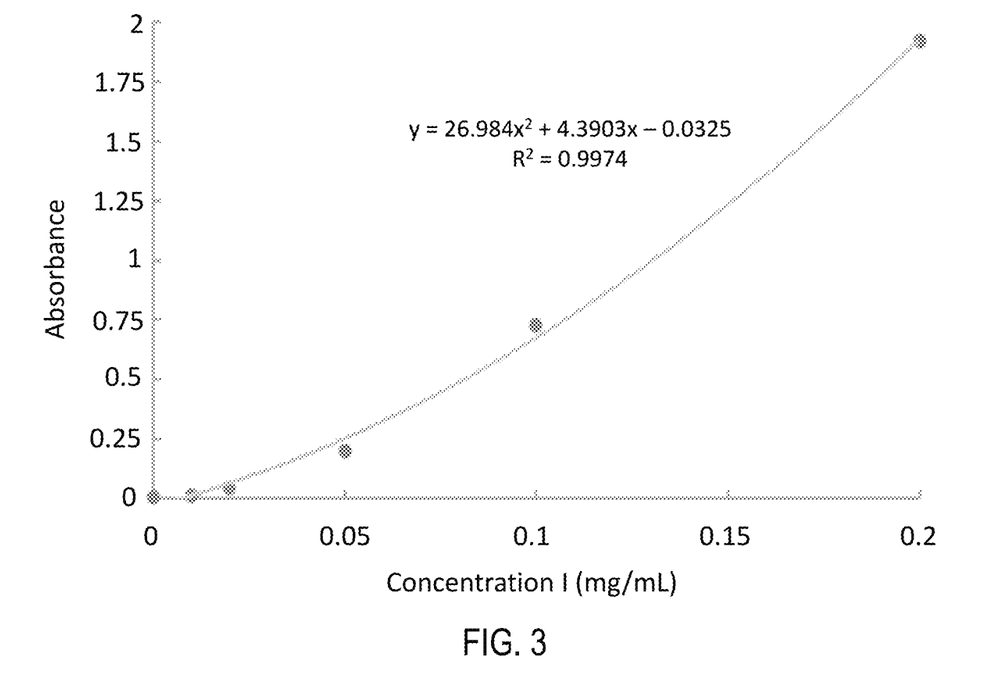
FIG. 3: UV-visible spectroscopy calibration: Absorbance (dimensionless) in function of concentration of iodine.
Figure 4:
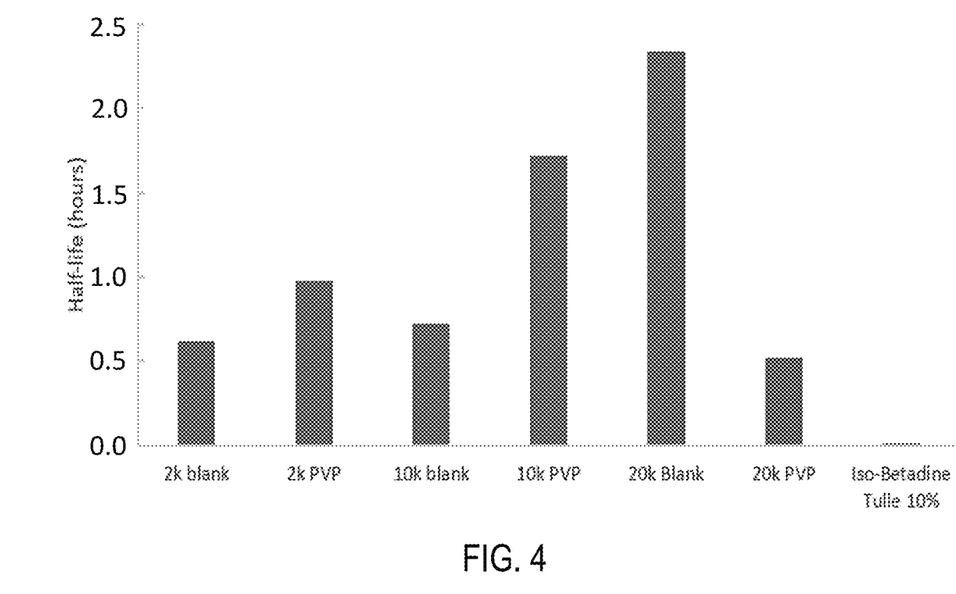
FIG. 4: The half-life (the time required for the leached concentration to decrease by half) of hydrogel samples and Iso-Betadine Tulle 10%.

FIG. 3 represents the UV-visible spectroscopy calibration expressed as Absorbance (dimensionless) in function of the concentration of iodine. FIG. 4 represents the half-life of hydrogel samples and Iso-Betadine Tulle 10%. From FIG. 4 we can conclude that all our formulations of our polymers have significantly higher half-life values than the standard used today namely Iso-Betadine Tulle 10%. All polymers/blends had at least half-life values of 30 min whereas Iso-Betadine Tulle 10% only had a half-life of 37 sec, meaning that all our materials released slower than the current standard. Within our polymers/blends it was noticeable that with the addition of PVP, the half-life was extended (thus release prolonged) except for the case of AUP 20k PVP. The best and most prolonged release was obtained with pure AUP20k.

Example 2

Gel Fraction & Swelling Ratio

Sample Preparation:

Mixtures containing 30 wt % AUP (of the respective molecular weight) and water were prepared (named 30 wt % AUP X kg/mol, w/o iodine), wherein X represents 2k, 4k or 8k.

Additionally, samples containing 30 wt % AUP (of the respective molecular weight), 0.6 wt % iodine and water were prepared mixing AUP, Lugol's solution and water (named 30 wt % AUP X kg/mol, with iodine).

The samples containing 2 kg/mol AUP were injected in glass molds with a diameter of 10 cm and 300 μm thickness to receive a polymer film with homogeny thickness. The other samples were coated with a doctor blade (gap width 1500 μm) on Teflon. Directly after preparation, the films were polymerized using the MEVEX electron accelerator. 2 kg/mol samples were irradiated with 30 kGy (once), 4 kg/mol a samples with 2×30 kGy and 8 kg/mol with 3×30 kGy.

For swelling/gel fraction tests, the samples were dried for 24 h directly after preparation and weighted (m$_{dry, before\ swelling}$) Afterwards, they were swollen for 5 days in water (m$_{after\ swelling}$) and dried again (m$_{dry, after\ swelling}$) The samples were stored at 8° C. after preparation.

Results:

$$\text{Gel fraction} = \frac{m_{dry, after\ swelling}}{m_{dry, before\ swelling}} \times 100\%;$$

$$\text{swelling ratio} = \frac{m_{after\ swelling}}{m_{dry, after\ swelling}} \times 100\%$$

| sample name | number | m (dry, before swelling) [g] | m (after swelling) [g] | m (dry, after swelling) [g] | swelling ratio [%] | STD | gel fraction [%] | STD |
|---|---|---|---|---|---|---|---|---|
| AUP 2 kDa w/o iodine | 1 | 0.0159 | 0.0758 | 0.0165 | 459% | 12% | 102% | 2% |
|  | 2 | 0.0184 | 0.0825 | 0.0186 |  |  |  |  |
|  | 3 | 0.0192 | 0.0908 | 0.0192 |  |  |  |  |
| AUP 4 kDa w/o iodine | 1 | 0.0279 | 0.2648 | 0.0271 | 980% | 3% | 95% | 2% |
|  | 2 | 0.0184 | 0.1662 | 0.0169 |  |  |  |  |
|  | 3 | 0.0245 | 0.2271 | 0.0232 |  |  |  |  |
| AUP 8 kDa w/o iodine | 1 | 0.0327 | 0.2911 | 0.0319 | 903% | 34% | 94% | 4% |
|  | 2 | 0.0302 | 0.2518 | 0.0268 |  |  |  |  |
|  | 3 | 0.0275 | 0.2271 | 0.0265 |  |  |  |  |
| AUP 2 kDa with iodine | 1 | 0.0113 | 0.0608 | 0.0105 | 600% | 16% | 93% | 0% |
|  | 2 | 0.0120 | 0.0670 | 0.0111 |  |  |  |  |
|  | 3 | 0.0138 | 0.0798 | 0.0129 |  |  |  |  |
| AUP 4 kDa with iodine | 1 | 0.0274 | 0.2452 | 0.0200 | 1292% | 52% | 70% | 4% |
|  | 2 | 0.0249 | 0.2450 | 0.0181 |  |  |  |  |
|  | 3 | 0.0143 | 0.1194 | 0.0092 |  |  |  |  |
| AUP 8 kDa with iodine | 1 | 0.0294 | 0.3066 | 0.0219 | 1446% | 39% | 72% | 2% |
|  | 2 | 0.0257 | 0.2672 | 0.0185 |  |  |  |  |
|  | 3 | 0.0235 | 0.2452 | 0.0164 |  |  |  |  |

Iodine Content of Dried Samples (by XPS)

Results were corrected by small percentages of silica and fluorine (from the silica wafer and Teflon matrix). Percentages of C, N and O are also given.

|  | 2 kDa | 4 kDa | 8 kDa |
|---|---|---|---|
| I | 0.2 at. % | 0.2 at. % | 0.2 at. % |
| C | 71.6 at. % | 74.6 at. % | 81.2 at. % |
| O | 26.7 at. % | 24.1 at. % | 17.5 at. % |
| N | 1.5 at. % | 1.1 at. % | 1.1 at. % |

Release:

Round discs of 1 cm diameter were prepared from each sample. Each sample was placed in 2 ml PBS buffer. The buffer was changed after 20, 40, 60, 90, 120, 150, 180 and 240 min and stored separated from each other.

200 μl of the buffer solution were injected in a 96 well microtiter plate. The absorbance of the buffer solutions at 350 nm was measured using a UVVIS microtiter plate reader from TECAN. 0.01% Lugol's solution (0.1 $I_2/I^-$ mg/ml) were used as reference.

The samples were yellow when the experiment started, but turned colorless after 40 min (for 4 and 8 kg/mol) or 90 min (2 kg/mol), respectively.

The results are as expected with an increasing swelling ratio with a higher molar mass of the backbone of the AUP. The addition of iodine to the AUP before e-beam treatment has especially an influence on the gel fraction of the higher molar mass backbones, but interestingly not on the AUP 2k.

Figure 5:
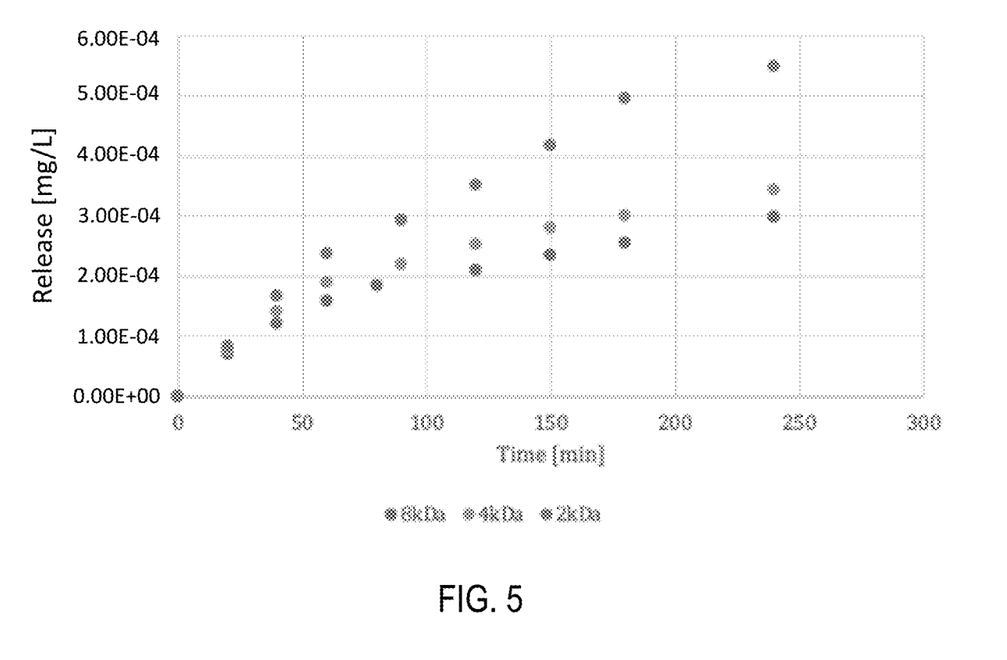
FIG. 5: Release of iodine from the AUP sheets over time.

When looking at the release. It is seen that especially the 8k has a stronger release, which could be partially explained by the higher (significant p<0.05) iodine content compared to the lower molar masses. Interestingly, the release is on a more controlled prolonged way, rather than the burst release of IBT as seen in FIG. 5.

|  | average concentration | standard deviation |
|---|---|---|
| IBT | 22.0475 | 0.526205 |
| 8k iodine | 17.545 | 1.584729 |
| 4k iodine | 12.96 | 1.083267 |
| 2k iodine | 11.45 | 0.8814 |

Example 3

Iodine Uptake as a Function of Spacer Type

Two 30% w/w AUP solutions made by dissolving 3 g AUP-PEG1k in 7 ml $H_2O$ and 3 g AUP-PCL1k in 4.697 ml $CHCl_3$, were subsequently poured between two parallel glass plates, which were coated with Teflon release foil and separated by a 3 mm thick silicone spacer, and crosslinked for 30 minutes of UV-A irradiation from both sides (365 nm, 14-15 mW/cm$^2$). From the resulting hydrogels 16 mm diameter samples were cut out and dried under vacuum except half of AUP-PEG1k samples.

To complex iodine to the hydrogel samples, a 1% Lugol's iodine solution was made by dissolving KI and I2 in a 1.576:1 weight ratio in Milli-Q® $H_2O$. Half of the AUP samples were pre-incubated for 2 days in Milli-Q® $H_2O$ before all samples were incubated in the iodine solution for 1 h, then removed from the solution, cut down to 12 mm and placed in a vacuum desiccator for 3 h.

A PANalytical ε-psilon3-XL with corresponding epsilon 3 software was used to determine the iodine content in hydrogel samples. The system parameters were a voltage of 12 kV, a current of 0.974 mA, an acquisition time of 200 seconds and an A1-50 filter.

|  | Avg. I count | Conc (mg/cm$^3$) |
|---|---|---|
| AUP-PCL1k_dry | 61190.66 | 74.85 |
| AUP-PEG1k_dry | 90751.34 | 111.32 |
| AUP-PCL1k_wet | 36338.02 | 44.33 |
| AUP-PEG1k_wet | 68398.90 | 83.84 |

We have compared iodine uptake for AUP1k with ethylene oxide versus caprolactone spacer both in dry and hydrated samples using XRF measurements (see table above). We have found substantially higher iodine values for the AUP consisting of the ethylene oxide spacer compared to the caprolactone spacer, irrespective of the iodine loading conditions (i.e. iodine loading in dry versus hydrated hydrogel films) for a polymer backbone molar mass of 1 kg/mol. The latter is surprising given the limited chain length of the spacer in contrast with the 1k AUP backbone. As a result, we have selected ethylene oxide as the preferred spacer for the present invention as a higher iodine loading capability results in superior antibacterial properties.

The invention claimed is:

1. A hydrogel comprising:
an antimicrobial agent; and
a cross-linkable urethane-based polymer represented by formula (I):

where:
each occurrence of X and Y is independently a moiety comprising one or more group chosen from acrylate groups, (multi)methacrylate groups, (multi)acrylate group, thiolactones, or thiol-ene crosslinkable groups;
each occurrence of Spacer is independently selected from the group consisting of oligo(ethylene oxide), oligo(propylene oxide), oligo(caprolactone), oligo(lactide), and oligo(glycolide);
m and n are each independently from 1 to 6;
p is from 1 to 10; and
each occurrence of Backbone is independently selected from the group consisting of polyethylene glycol), poly(vinyl pyrrolidone), poly(N-vinyl caprolactam), and combinations thereof.

2. The hydrogel of claim 1, wherein each occurrence of Spacer is oligo(ethylene) oxide.

3. The hydrogel of claim 1, comprising a polymer combination of cross-linkable urethane-based polymers represented by formula (I), wherein Backbone of at least one polymer of the polymer combination is poly(ethylene glycol) and Backbone of at least one other polymer of the polymer combination comprises poly(vinyl pyrrolidone), poly(N-vinyl caprolactam), or a combination thereof.

4. The hydrogel of claim 3, wherein the polymer combination is selected from a copolymer, a polymer blend, or a combination of different polymer layers.

5. The hydrogel of claim 1, wherein each occurrence of Backbone is independently selected from the group consisting of
poly(ethylene glycol) having a molecular weight from about 400 g/mol to about 20,000 g/mol,
poly(vinyl pyrrolidone) having a molecular weight from about 400 g/mol to about 365,000 g/mol,
poly(N-vinyl caprolactam) having a molecular weight from about 100 g/mol to about 2,500,000 g/mol, and
combinations thereof.

6. The hydrogel of claim 5, wherein each occurrence of Spacer is oligo(ethylene) oxide.

7. The hydrogel of claim 1, wherein Backbone comprises poly(ethylene glycol) having a molecular weight from about 400 g/mol to about 20000 g/mol.

8. The hydrogel of claim 1, wherein Backbone comprises polyvinyl pyrrolidone) having a molecular weight from about 400 g/mol to about 365,000 g/mol.

9. The hydrogel of claim 1, wherein Backbone comprises poly(N-vinyl caprolactam) having a molecular weight from about 400 g/mol to about 2,500,000 g/mol.

10. The hydrogel of claim 1, further comprising free polyvinyl pyrrolidone), free polyethylene glycol), free poly (N-vinyl caprolactam), or a combination thereof.

11. The hydrogel of claim 1, wherein the antimicrobial agent is an iodine-based agent.

12. The hydrogel of claim 1, wherein the hydrogel is in the form of a sheet, a membrane, a fiber, a particle, or a scaffold.

13. A wound dressing comprising the hydrogel of claim 1.

14. A crosslinked hydrogel obtained from chemically crosslinking the cross-linkable urethane-based polymer represented by formula (I) of a hydrogel according to claim 1.

15. A wound dressing comprising the crosslinked hydrogel of claim 14.

* * * * *